United States Patent
Tralshawala et al.

(10) Patent No.: US 9,494,490 B2
(45) Date of Patent: Nov. 15, 2016

(54) CREEP LIFE MANAGEMENT SYSTEM FOR A TURBINE ENGINE AND METHOD OF OPERATING THE SAME

(75) Inventors: Nilesh Tralshawala, Rexford, NY (US); Harold Edward Miller, Glenville, NY (US); Vivek Venugopal Badami, Schenectady, NY (US); Sameer Vittal, Atlanta, GA (US); Daniel White Sexton, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 810 days.

(21) Appl. No.: 13/585,194

(22) Filed: Aug. 14, 2012

(65) Prior Publication Data

US 2014/0052410 A1    Feb. 20, 2014

(51) Int. Cl.
*G01M 15/14* (2006.01)
*F01D 17/04* (2006.01)
*F01D 21/00* (2006.01)

(52) U.S. Cl.
CPC .............. *G01M 15/14* (2013.01); *F01D 17/04* (2013.01); *F01D 21/003* (2013.01); *F05D 2270/332* (2013.01); *F05D 2270/808* (2013.01); *G01N 2203/0071* (2013.01); *G01N 2203/0244* (2013.01)

(58) Field of Classification Search
CPC ....................... G01N 2203/0244; F01D 17/04
USPC ........................................................... 702/183
See application file for complete search history.

(56) References Cited

U.S. PATENT DOCUMENTS

| | | | |
|---|---|---|---|
| 7,368,827 B2 | 5/2008 | Kulkarni et al. | |
| 7,810,385 B1 | 10/2010 | Narcus | |
| 7,969,323 B2 | 6/2011 | Mitchell et al. | |
| 2008/0316109 A1* | 12/2008 | Savolainen | 343/700 MS |
| 2011/0137575 A1* | 6/2011 | Koul | 702/34 |
| 2013/0332025 A1* | 12/2013 | Ziarno | 701/33.4 |

\* cited by examiner

*Primary Examiner* — Manuel Rivera Vargas
(74) *Attorney, Agent, or Firm* — Armstrong Teasdale LLP

(57) ABSTRACT

A creep life management system includes at least one sensor apparatus coupled to a first component. The at least one sensor apparatus is configured with a unique identifier. The creep life management system also includes at least one reader unit coupled to a second component. The at least one reader unit is configured to transmit an interrogation request signal to the at least one sensor apparatus and receive a measurement response signal transmitted from the at least one sensor apparatus. The creep life management system further includes at least one processor programmed to determine a real-time creep profile of the first component as a function of the measurement response signal transmitted from the at least one sensor apparatus.

20 Claims, 9 Drawing Sheets

CREEP LIFE MANAGEMENT SYSTEM FOR A TURBINE ENGINE AND METHOD OF OPERATING THE SAME

STATEMENT REGARDING FEDERALLY SPONSORED RESEARCH & DEVELOPMENT

This invention was made with Government support under contract number DE-FC26-05NT42643 awarded by the Department of Energy (DOE). The Government has certain rights in this invention.

BACKGROUND OF THE INVENTION

The embodiments described herein relate generally to condition monitoring of systems and equipment, and more particularly, to a method and system for use in condition monitoring of turbomachines.

At least some known turbomachines, i.e., gas turbine engines compress air via a plurality of rotatable compressor blades and ignite a fuel-air mixture in a combustor to generate combustion gases that are channeled through rotatable turbine buckets via a hot gas path. Also, at least some other known turbomachines, i.e., steam turbine engines channel steam through rotatable buckets via a steam path. Such known turbomachines convert thermal energy of the combustion gas stream and steam to mechanical energy used to rotate a turbine shaft. Output of the turbomachines may be used to power a machine, for example, an electric generator, a compressor, or a pump.

Many known compressor blades and turbine buckets are manufactured via processes that facilitate production of such blades and buckets with consistent material properties between like units thereof. However, slight material variations in the blades' and buckets' material properties may be present and are difficult to detect. Once these blades and buckets are placed in service, these minute differences start creating variations in the remaining useful life (RUL) of the blades and buckets.

At least some known maintenance repair processes for turbomachine components such as blades and buckets use standardized inspection and repair methods that are applied to all similar pieces of equipment to process the equipment through a standardized workscope. Such standardized workscopes may include turbomachine disassembly, extensive inspections, and corrective repair procedures that are applied to each component regardless of the actual condition of each component. For example, a component model that is constructed to predict life for the component may determine a replacement schedule and these values are used to schedule replacements. As a result, components having little or no defects may be processed with a similar expenditure of resources as those components having significant defects, including unnecessary replacement. This expenditure of resources is considered to be suboptimal from a financial perspective.

Also, at least some known maintenance repair processes for turbomachine components may include uncertainties of results for inspections that include standard non-destructive examination (NDE) and subsequent data analysis. For example, many known NDE processes/analyses do not provide adequate correlations of crack-growth data, including crack-growth rates, as a function of creep and creep-fatigue. In addition, there are few, if any, mechanisms to characterize crack-growth rates to specific components. Therefore, it is difficult to determine a RUL of a component undergoing progressive creep. Creep is estimated by measuring dimensions of the components and tracking changes of the dimensions over time. Record keeping practices are not standardized and frequently, due to uncertainties regarding original dimensions of the components and subsequent measurements, accurate determinations of creep are difficult to make.

Further, at least some known measurement systems for operating turbines and compressors include measurement instruments coupled to the compressor blades and turbine buckets. These systems typically require extensive wiring, modifications to the blades and buckets to accommodate the wiring, and complicated slip ring configurations, that are necessary due to the rotational operation of the monitored components, to transmit measurement data from the blades and buckets to an external data storage and analysis unit. Therefore, such systems increase construction and maintenance costs.

BRIEF SUMMARY OF THE INVENTION

In one aspect, a creep life management system is provided. The creep life management system includes at least one sensor apparatus coupled to a first component. The at least one sensor apparatus is configured with a unique identifier. The creep life management system also includes at least one reader unit coupled to a second component. The at least one reader unit is configured to transmit an interrogation request signal to the at least one sensor apparatus and receive a measurement response signal transmitted from the at least one sensor apparatus. The creep life management system further includes at least one processor programmed to determine a real-time creep profile of the first component as a function of the measurement response signal transmitted from the at least one sensor apparatus.

In a further aspect, a method of operating a turbine engine is provided. The turbine engine includes at least one rotatable component, at least one stationary component, and a creep life management system including a first portion coupled to the at least one rotatable component and a second portion coupled to the at least one stationary component. The method includes rotating the at least one rotatable component with respect to the at least one stationary component and interrogating the first portion by the second portion. The method also includes transmitting from the first portion a response signal in response to the interrogation by the second portion, wherein the response signal is representative of a measurement of the at least one rotatable component. The method further includes receiving the response signal at the second portion and determining a unique creep profile for the at least one rotating component that is at least partially based on the response signal.

In another aspect, a turbine engine is provided. The turbine engine includes at least one rotatable component and at least one stationary component. The turbine engine also includes a creep life management system that includes at least one sensor apparatus coupled to the at least one rotatable component. The at least one sensor apparatus is configured with a unique identifier. The creep life management system also includes at least one reader unit coupled to the at least one stationary component. The at least one reader unit is configured to transmit an interrogation request signal to the at least one sensor apparatus and receive a measurement response signal from the at least one sensor apparatus. The creep life management system further includes at least one processor programmed to determine a real-time creep profile of said at least one rotatable component as a function of the measurement response signal transmitted from the at least one sensor apparatus.

DETAILED DESCRIPTION OF THE INVENTION

Figure 1:
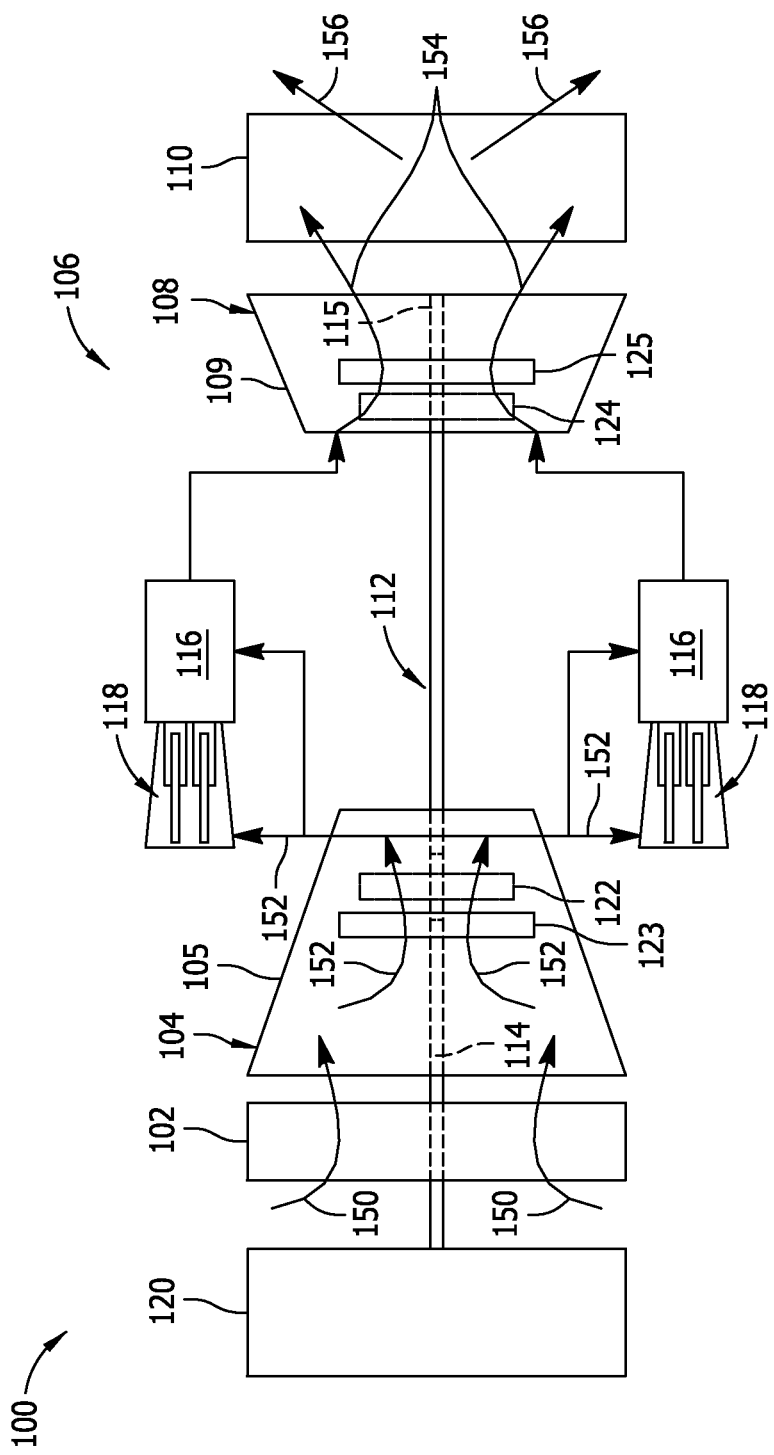
FIG. 1 is schematic diagram of an exemplary gas turbine engine.

FIG. 1 is a schematic view of a rotary machine 100, i.e., a turbomachine, and more specifically, a turbine engine. In the exemplary embodiment, turbine engine 100 is a gas turbine engine. Alternatively, turbine engine 100 is any other turbine engine and/or rotary machine, including, without limitation, a steam turbine engine. In the exemplary embodiment, gas turbine engine 100 includes an air intake section 102, and a compressor section 104 that is coupled downstream from, and in flow communication with, intake section 102. Compressor section 104 is enclosed within a compressor casing 105. A combustor section 106 is coupled downstream from, and in flow communication with, compressor section 104, and a turbine section 108 is coupled downstream from, and in flow communication with, combustor section 106. Turbine engine 100 is enclosed within a turbine casing 109 and includes an exhaust section 110 that is downstream from turbine section 108. Moreover, in the exemplary embodiment, turbine section 108 is coupled to compressor section 104 via a rotor assembly 112 that includes, without limitation, a compressor rotor, or drive shaft 114 and a turbine rotor, or drive shaft 115.

In the exemplary embodiment, combustor section 106 includes a plurality of combustor assemblies, i.e., combustors 116 that are each coupled in flow communication with compressor section 104. Combustor section 106 also includes at least one fuel nozzle assembly 118. Each combustor 116 is in flow communication with at least one fuel nozzle assembly 118. Moreover, in the exemplary embodiment, turbine section 108 and compressor section 104 are rotatably coupled to a load 120 via drive shaft 114. For example, load 120 may include, without limitation, an electrical generator and/or a mechanical drive application, e.g., a pump. Alternatively, gas turbine engine 100 may be an aircraft engine. In the exemplary embodiment, compressor section 104 includes at least one compressor blade assembly 122, i.e., blade 122 and at least one adjacent stationary vane assembly 123.

Also, in the exemplary embodiment, turbine section 108 includes at least one turbine blade assembly, i.e., bucket 124 and at least one adjacent stationary nozzle assembly 125. Each compressor blade assembly 122 and each turbine bucket 124 is coupled to rotor assembly 112, or, more specifically, compressor drive shaft 114 and turbine drive shaft 115.

In operation, air intake section 102 channels air 150 towards compressor section 104. Compressor section 104 compresses inlet air 150 to higher pressures and temperatures prior to discharging compressed air 152 towards combustor section 106. Compressed air 152 is channeled to fuel nozzle assembly 118, mixed with fuel (not shown), and burned within each combustor 116 to generate combustion gases 154 that are channeled downstream towards turbine section 108. Combustion gases 154 generated within combustors 116 are channeled downstream towards turbine section 108. After impinging turbine bucket 124, thermal energy is converted to mechanical rotational energy that is used to drive rotor assembly 112. Turbine section 108 drives compressor section 104 and/or load 120 via drive shafts 114 and 115, and exhaust gases 156 are discharged through exhaust section 110 to ambient atmosphere.

Figure 2:
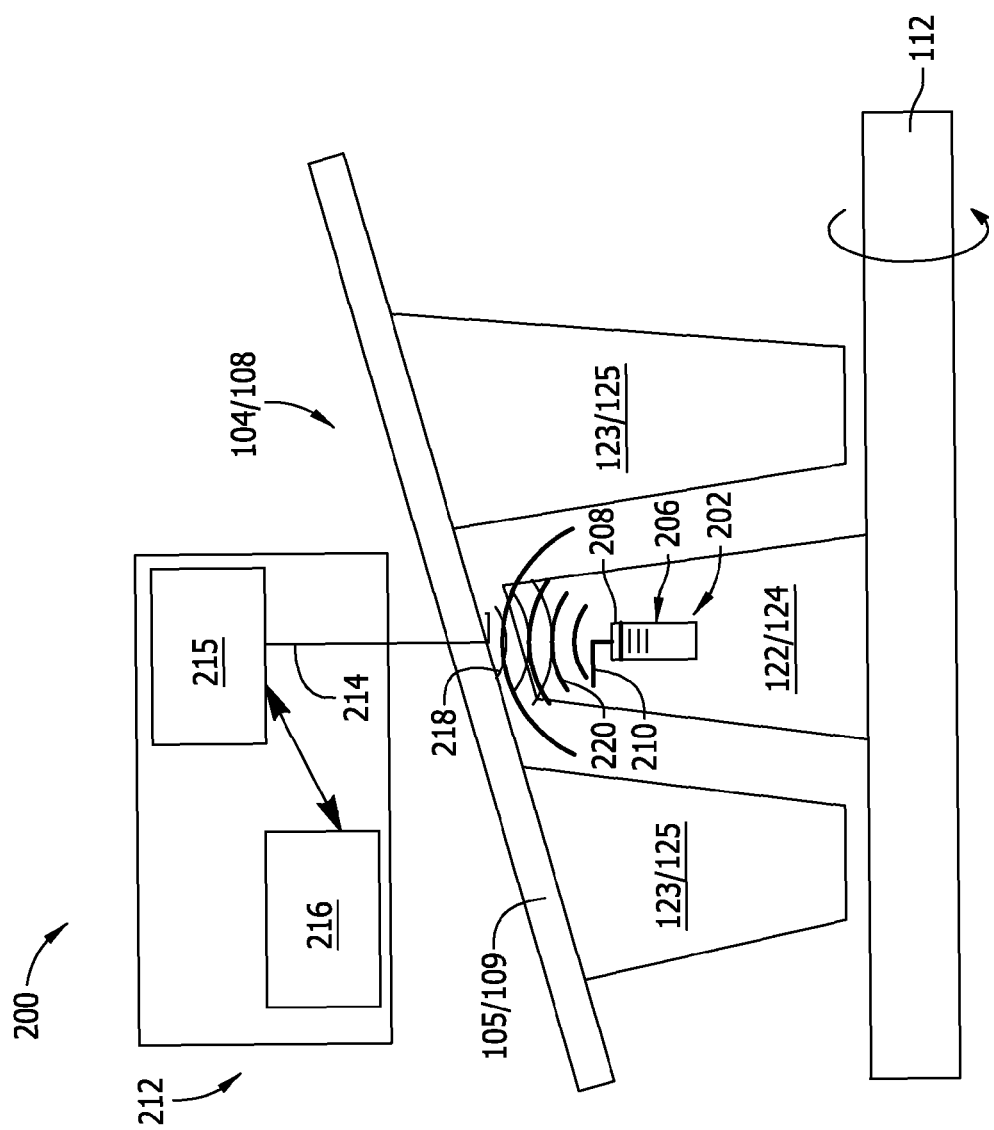
FIG. 2 is a schematic view of an exemplary creep life management system that may be used with the gas turbine engine shown in FIG. 1.

FIG. 2 is a schematic view of an exemplary creep life management system 200 that may be used with gas turbine engine 100 (shown in FIG. 1). Creep life management system 200 includes at least one sensor apparatus 202 coupled to one of compressor blade 122 and turbine bucket 124. In the exemplary embodiment, sensor apparatus 202 is a surface acoustic wave (SAW) sensor apparatus. Alternatively, sensor apparatus 202 is any sensing device that is configured to withstand substantially constant exposure to a harsh environment, such harsh environment may include, without limitation, high-temperature compressed air in excess of 100 degrees Celsius (° C.) (212 degrees Fahrenheit (° F.)), high-temperature combustion gases in excess of 260° C. (500° F.), and significant rotational forces induces by rotational velocities of approximately 3000 revolutions per minute (rpm) to approximately 3600 rpm. Such alternative sensing devices may include, without limitation, direct-deposited (DD) RF sensor apparatus.

Also, in the exemplary embodiment, each sensor apparatus 202 includes a piezoelectric crystal substrate 204. Sensor apparatus 202 also includes a plurality of reflectors 206 coupled to piezoelectric substrate 204. Reflectors 206 facilitate providing each sensor apparatus 202 with a unique identifier such that unique identification of each compressor blade 122 and each turbine bucket 124 is facilitated through associated sensor apparatus 202 coupled thereto. Alternatively, sensor apparatus 202 includes any unique identification mechanisms, including, without limitation, devices similar to retail RF-identification (RFID) devices, wherein such RFID devices include a uniquely configured RF transducer. Sensor apparatus 202 also includes at least one interdigital transducer 208 coupled to piezoelectric substrate 204. Sensor apparatus 202 further includes at least one antenna 210 coupled to interdigital transducer 208. Moreover, sensor apparatus 202 is passive, i.e., it includes no on-board power supplies and is in a dormant condition until it is interrogated as described below.

Further, in the exemplary embodiment, creep life management system 200 includes a reader unit 212. Reader unit 212 is coupled to a stationary portion of gas turbine engine 100. Reader unit 212 includes at least one antenna 214, at least one radio frequency (RF) transmitter device and at least one RF receiver device coupled to antenna 214. In the exemplary embodiment, the RF transmitter and receiver devices are integrated into a transceiver device 215.

Moreover, in the exemplary embodiment, reader unit 212 includes a controller 216 coupled to transceiver device 215. Alternatively, controller 216 may be external to reader unit 212. Controller 216 includes and/or is implemented by at least one processor (not shown). As used herein, the processor includes any suitable programmable circuit such as, without limitation, one or more systems and microcontrollers, microprocessors, a general purpose central processing unit (CPU), reduced instruction set circuits (RISC), application specific integrated circuits (ASIC), programmable logic circuits (PLC), field programmable gate arrays (FPGA), and/or any other circuit capable of executing the functions described herein. The above examples are exemplary only, and thus are not intended to limit in any way the definition and/or meaning of the term "processor."

In addition, controller 216 includes at least one memory device (not shown) coupled to the processor that stores computer-executable instructions and data, such as operating data, parameters, setpoints, threshold values, and/or any other data that enables creep life management system 200 to function as described herein. The memory device may include one or more tangible, non-transitory, computer readable media, such as, without limitation, random access memory (RAM), dynamic random access memory (DRAM), static random access memory (SRAM), a solid state disk, a hard disk, read-only memory (ROM), erasable programmable ROM (EPROM), electrically erasable programmable ROM (EEPROM), and/or non-volatile RAM (NVRAM) memory.

The methods described herein may be encoded as executable instructions and algorithms embodied in a tangible, non-transitory, computer readable medium, including, without limitation, a storage device and/or a memory device. Such instructions and algorithms, when executed by a processor, cause the processor to perform at least a portion of the methods described herein. Moreover, as used herein, the term "non-transitory computer-readable media" includes all tangible, computer-readable media, such as a firmware, physical and virtual storage, CD-ROMs, DVDs and another digital source such as a network or the Internet, as well as yet to be developed digital means, with the sole exception being a transitory, propagating signal.

In operation, gas turbine engine 100 is in service and turbine section 108 drives compressor section 104 via rotor assembly 112 such that compressor blades 122 and turbine buckets 124 are rotating. Reader unit 212 transmits at least one RF request signal 218 via antenna 214, i.e., controller 216 commands transceiver device 215 to interrogate each sensor apparatus 202 as each apparatus 202 rotates by antenna 214. Request signal 218 is received by antenna 210 and the energy in signal 218 is transmitted to interdigital transducer 208. Interdigital transducer 208 induces a surface acoustic wave in piezoelectric substrate 204. The resonant frequency of the surface acoustic wave is influenced by reflectors 206 and real-time characteristics of associated compressor blade 122 or turbine bucket 124, e.g., temperature and strain. Interdigital transducer 208 converts the energy with the resonant frequency into an RF response signal 220 that is transmitted to reader unit 212 via antennas 210 and 214 and transceiver device 215. Data within response signal 220 is evaluated by controller 216.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Figure 3:
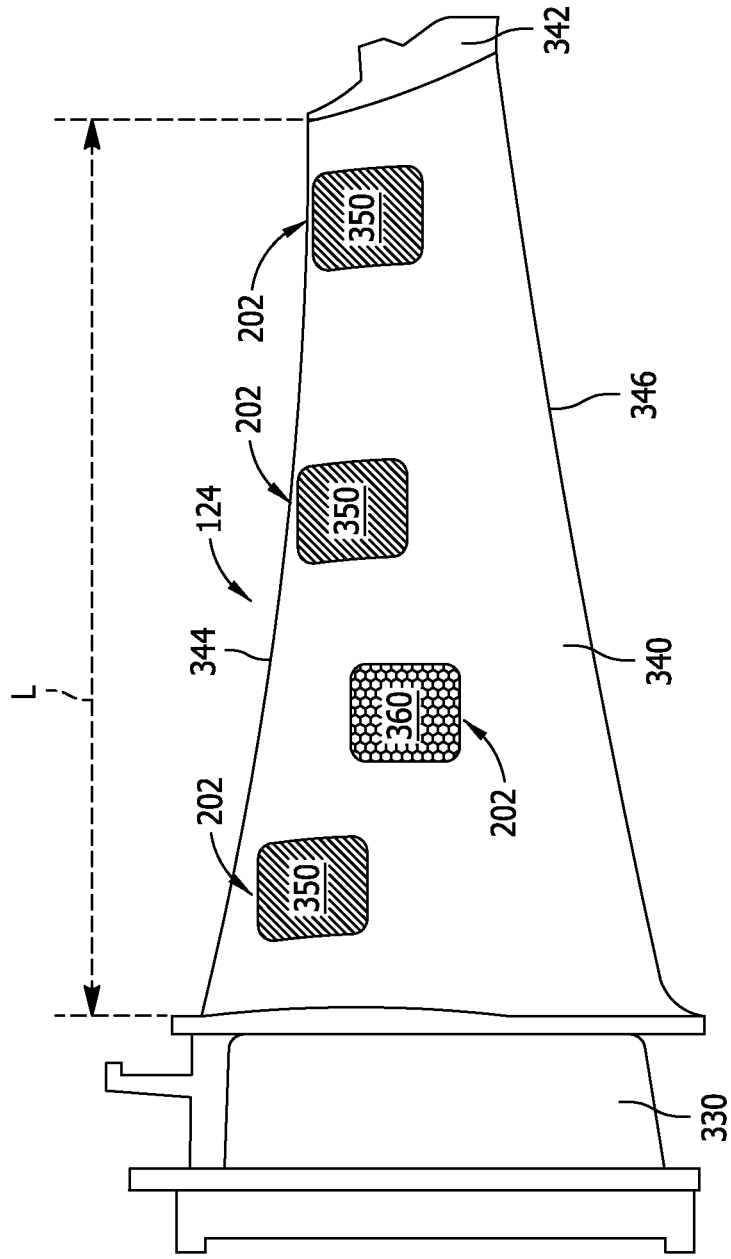
FIG. 3 is a schematic view of an exemplary turbine bucket with a plurality of sensors coupled thereto that may be used with the gas turbine engine shown in FIG. 1.

FIG. 3 is a schematic view of exemplary turbine bucket 124 with sensor apparatus 202 coupled thereto that may be used with gas turbine engine 100 (shown in FIG. 1). Turbine bucket 124 includes a root portion 330 and an airfoil portion 340 coupled to root portion 330. Airfoil portion 340 defines an airfoil tip portion 342, a leading edge 344, a trailing edge 346, and a length L between root portion 330 and airfoil tip portion 342. In the exemplary embodiment, sensor apparatus 202 includes a plurality of temperature sensors 350 positioned proximate leading edge 344, i.e., the portion of buckets 124 that first receive high-temperature combustion gases 154 (shown in FIG. 1). Also, temperature sensors 350 are positioned within predetermined percentile ranges of length L, e.g., approximately between 10% and 20%, 45% and 55%, and 85% and 95%. Alternatively, temperature sensors 350 are positioned anywhere on bucket 124 with any spacing therebetween that enables operation of creep life management system 200 (shown in FIG. 2) as described herein. Temperature sensors 350 are coupled to bucket 124 through any methods that enable operation of creep life management system 200 as described herein, including, without limitation, embedding of temperature sensors 350 within a substrate and/or a coating (neither shown) of airfoil 340, and mechanical coupling to a surface of the substrate and/or coating of airfoil 340.

Also, in exemplary embodiment, sensor apparatus 202 includes a strain sensor 360. Strain sensor 360 is positioned between percentile ranges of length L of approximately 30%-40%. Alternatively, any number of strain sensors 360 are positioned anywhere on bucket 124 with any spacing therebetween that enables operation of creep life management system 200 as described herein. Temperature sensors 350 are coupled to bucket 124 through any methods that enable operation of creep life management system 200 as described herein, including, without limitation, those described for temperatures sensors 350.

Temperature sensors 350 and strain sensors 360 are similar to sensor apparatus 202 (shown in FIG. 2) and include at least one antenna 210 (shown in FIG. 2).

Figure 4:
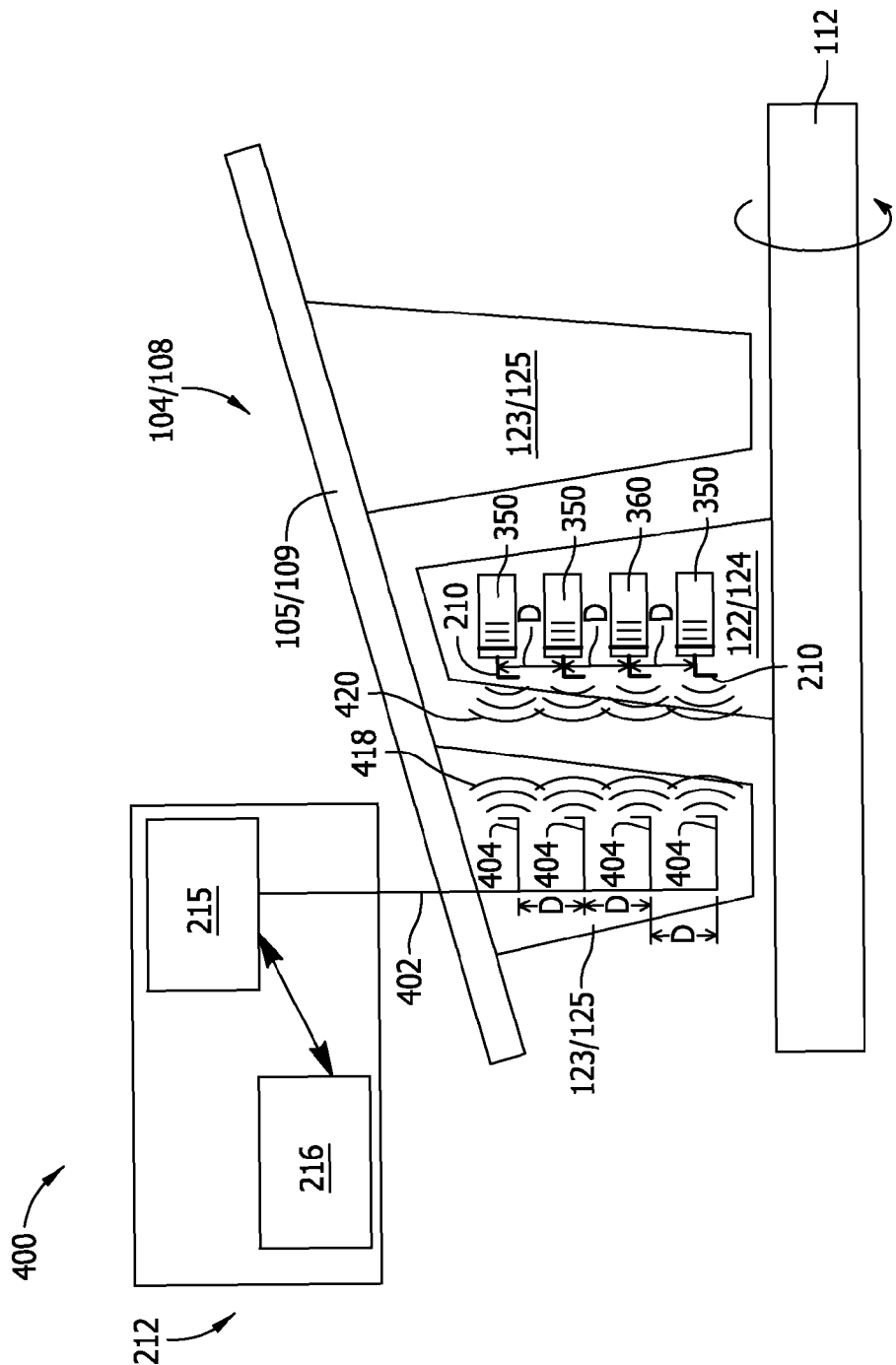
FIG. 4 is a schematic view of an alternative exemplary creep life management system that may be used with the gas turbine engine shown in FIG. 1.

FIG. 4 is a schematic view of an alternative exemplary creep life management system 400 that may be used with gas turbine engine 100 (shown in FIG. 1). System 400 is similar to system 200 (shown in FIG. 2) with the exception that system 400 includes an antenna extension 402 coupled to transceiver device 215. Also, antenna extension 402 penetrates and extends through either of compressor casing 105 and turbine casing 109. Further, four antenna 404 are fixedly coupled to antenna extension 402 and are fixedly coupled to either one of stationary vane assembly 123 and stationary nozzle assembly 125. Moreover, system 400 includes a plurality of temperature sensors 350 and a strain sensor 360 coupled to one of blade 122 and bucket 124 in a configuration similar to that described above (shown in FIG. 3). In some embodiments, each antenna 404 is dedicated to, and communicatively coupled with, an antenna 210 associated with one of temperature sensors 350 and strain sensor 360 in one of a one-to-one relationship. In some other embodiments, each antenna 404 is dedicated to, and communicatively coupled with, an antenna 210 associated with more than one of temperature sensors 350 and/or strain sensor 360 in a one-to-many relationship. Antenna extension 402 is configured with a plurality of interrogation channels (not shown), i.e., one channel per one sensor 350/360. Alternatively, antenna extension 402 is configured with a single channel configured to transmit a plurality of signals, each with a unique coded identifier and/or frequency. Also, alternatively, any combination and any number of antennas 404, communication channels within antenna extension 402, and sensors 350 and 360 that enable operation of creep life management system 400 as described herein is used.

In operation, gas turbine engine 100 (shown in FIG. 1) is in service and turbine section 108 drives compressor section 104 via rotor assembly 112 such that compressor blades 122 and turbine buckets 124 are rotating. Reader unit 212 transmits at least one RF request signal 418 via at least one antenna 404, i.e., controller 216 commands transceiver device 215 to interrogate each sensor apparatus 350/360 as each apparatus 350/360 rotates by associated stationary antenna 404. Each request signal 418 is received by the associated sensor apparatus 350/360 and real-time characteristics of associated compressor blade 122 or turbine bucket 124, e.g., temperature and strain, are measured. An RF response signal 420 is transmitted to reader unit 212 via antennas 404 and transceiver device 215. Data within response signal 420 is evaluated by controller 216.

In the exemplary embodiment, antennas 210 are separated from each other at a distance D. Distance D is substantially equivalent to at least ¼ of the associated operational wavelength of RF response signals 420. Alternatively, distance D is equal to, or greater than, the spatial coherence distance of the wireless channel between sensor antennas 210 and reader antennas 404. Similarly, in the exemplary embodiment, antennas 404 are separated from each other at a distance D, i.e., either at least ¼ of the associated operational wavelength of RF response signals 420 or greater than the associated spatial coherence distance of the wireless channel between sensor antennas 210 and reader antennas 404. Such spatial separation of distance D between antennas 210 and antennas 404 facilitate receiving and processing RF response signals 420 by reader unit 212 such that the effects of RF multipath interference and independent receiver noise sources are significantly reduced and the overall signal levels of RF response signals 420 are boosted, thereby increasing system 400's sensitivity and the robustness of the readings.

Figure 5:
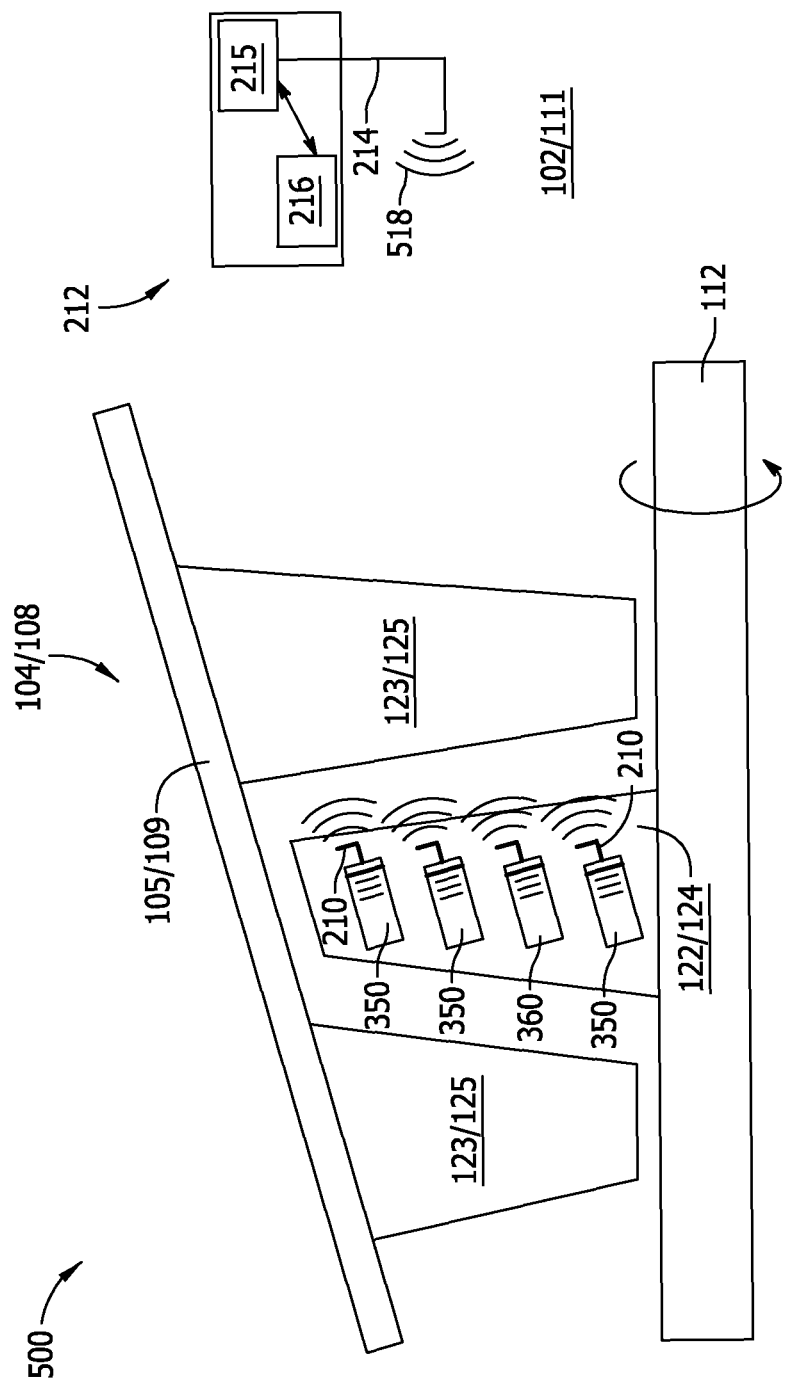
FIG. 5 is a schematic view of another alternative exemplary creep life management system that may be used with the gas turbine engine shown in FIG. 1.

FIG. 5 is a schematic view of another alternative exemplary creep life management system 500 that may be used with gas turbine engine 100 (shown in FIG. 1). System 500 is similar to systems 200 and 400 (shown in FIGS. 2 and 4, respectively) in that system 500 includes one antenna 214 (similar to system 200) coupled to transceiver device 215 and further coupled in communication with a plurality of temperature sensors 350 and a strain sensor 360 to one of blade 122 and bucket 124 (similar to system 400). System 500 differs from systems 200 and 400 with respect to reader unit 212, including, antenna 214, transceiver device 215, and controller 216. Reader 212 is positioned in one of air intake section 102 and exhaust section 110 and coupled to a stationary structure there (not shown in FIG. 5) such that there are no penetrations of either compressor casing 105 or turbine casing 109. Also, reader antenna 214 is communicatively coupled to the plurality of sensor apparatus antennas 210 in a one-to-many relationship. Alternatively, rather than a single reader antenna 214, reader unit 212 may include multiple reader antennas 214 that are separated by distance D (shown in FIG. 4) such that the effects of RF multipath interference and independent receiver noise sources are significantly reduced (as described above).

In operation, gas turbine engine 100 (shown in FIG. 1) is in service and turbine section 108 drives compressor section 104 via rotor assembly 112 such that compressor blades 122 and turbine buckets 124 are rotating. Reader unit 212 transmits at least one RF request signal 518 via antenna 214, i.e., controller 216 commands transceiver device 215 to interrogate each sensor apparatus 350/360 as each apparatus 350/360 rotates by associated stationary antenna 214. Each request signal 518 is received by the associated sensor apparatus 350/360 and real-time characteristics of associated compressor blade 122 or turbine bucket 124, e.g., temperature and strain, are measured. An RF response signal 520 is transmitted to reader unit 212 via antenna 214 and transceiver device 215. Data within response signal 520 is evaluated by controller 216.

Figure 6:
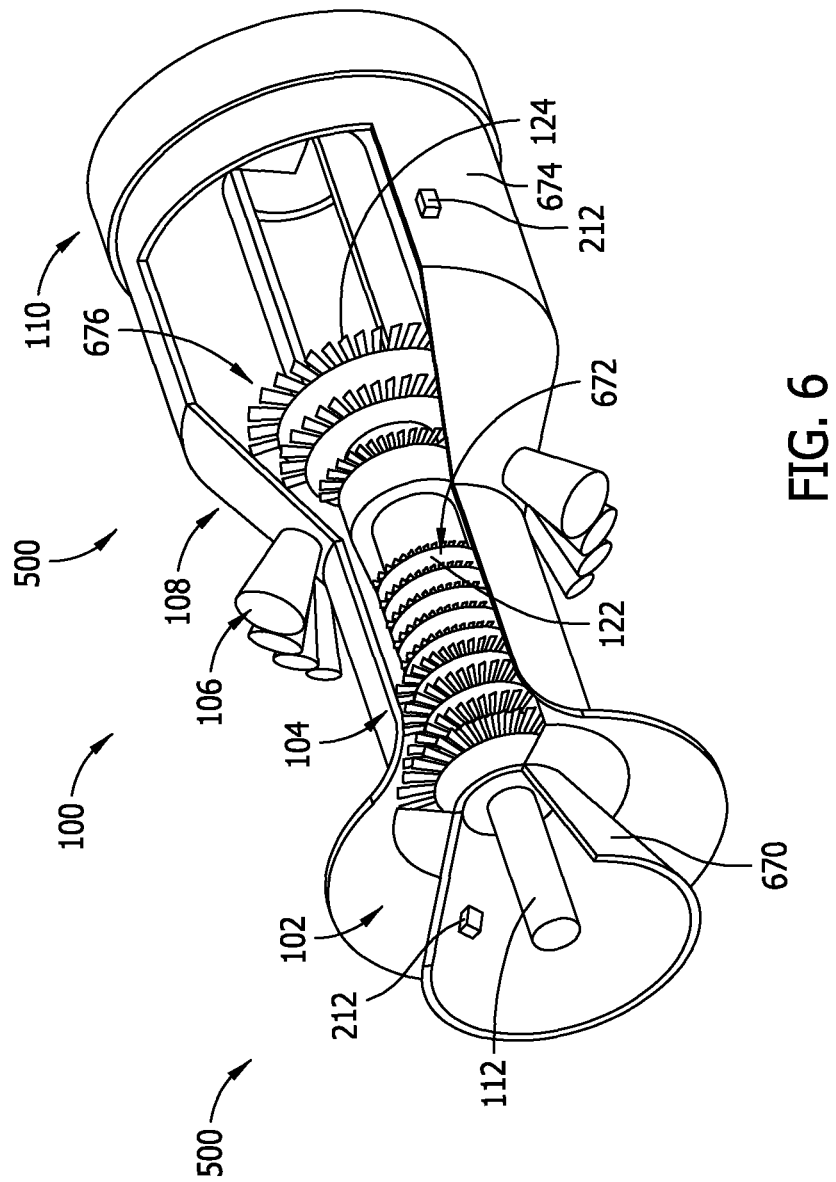
FIG. 6 is a schematic view of an exemplary positioning of portions of the creep life management systems shown in FIGS. 2, 4, and 5 within the gas turbine engine shown in FIG. 1.

FIG. 6 is a schematic view of an exemplary positioning of portions of creep life management system 500 within gas turbine engine 100. In the exemplary embodiment, reader unit 212 is positioned on a stationary portion of compressor section 104, i.e., at least one reader unit 212 is coupled to a compressor intake wall 670. Alternatively, reader units 212 are positioned anywhere that enables operation of creep life management system 500 as described herein. For example, without limitation, reader units 212 may be positioned anywhere within wireless RF communication range of associated sensor apparatus 202.

Also, in the exemplary embodiment, a plurality of sensor apparatus 202 (shown in FIGS. 2 and 3) are coupled to every compressor blade 122 in a last stage 672 of compressor section 104. Last stage 672 of compressor section 104 is typically exposed to compressed air 152 (shown in FIG. 1) at its highest pressures and temperatures prior to channeling into combustor section 106. At least one of each of temperature sensors 350 and strain sensor 360 is coupled to each blade 122 and each of sensors 350 and 360 on each blade 122 includes a unique alpha-numeric identification code. Alternatively, any configuration of sensor apparatus 202 is used on any stage of compressor section 104 that enables operation of creep life management system 500 as described herein.

Further, in the exemplary embodiment, reader unit 212 is positioned on a stationary portion of exhaust section 110, i.e., at least one reader unit 212 is coupled to a turbine exhaust wall 674. Alternatively, reader units 212 are positioned anywhere that enables operation of creep life management system 500 as described herein. For example, without limitation, reader units 212 may be positioned anywhere within wireless RF communication range of associated sensor apparatus 202.

Also, in the exemplary embodiment, a plurality of sensor apparatus 202 are coupled to every turbine bucket 124 in a last stage 676 of turbine section 108. Third, or last stage 676 of turbine section 108 is typically exposed to combustion gases 154 (shown in FIG. 1) at their lowest pressures and temperatures prior to channeling into exhaust section 110. At least one of each of temperature sensors 350 and strain sensor 360 is coupled to each bucket 124 and each of sensors 350 and 360 on each bucket 124 includes a unique alpha-numeric identification code. Alternatively, any configuration of sensor apparatus 202 is used on any stage of turbine section 108 that enables operation of creep life management system 200 as described herein.

In operation, each reader unit 212 interrogates each associated sensor apparatus 202 at predetermined intervals. For example, without limitation, each individual bucket 124 with at least one sensor apparatus 202 coupled thereto is interrogated by associated reader unit 212 once every hour while in operation, wherein each sensor apparatus 202 is interrogated in one second intervals. Therefore, for those turbine sections 108 having 91 buckets 124 with sensor apparatus 202, one cycle of data collection from buckets 124 is approximately 91 seconds in length. Sensor apparatus 202 can be interrogated and transmit a response regardless of the operating rotational velocity of gas turbine engine 100. Moreover, an operator may manually induce a data collection episode for any blade 122 and bucket 124 with sensor apparatus 202 through use of the unique identifier. Furthermore, data collection may be substantially continuous.

In alternative embodiments, system 400 (shown in FIG. 4) or system 500 may be substituted for system 200 (shown in FIG. 2). Also, in alternative embodiments, systems 200, 400, and 500 include any configuration that enables operation of such systems 200, 400, and 500 consistent with the specific configuration of gas turbine engine 100.

Figure 7:
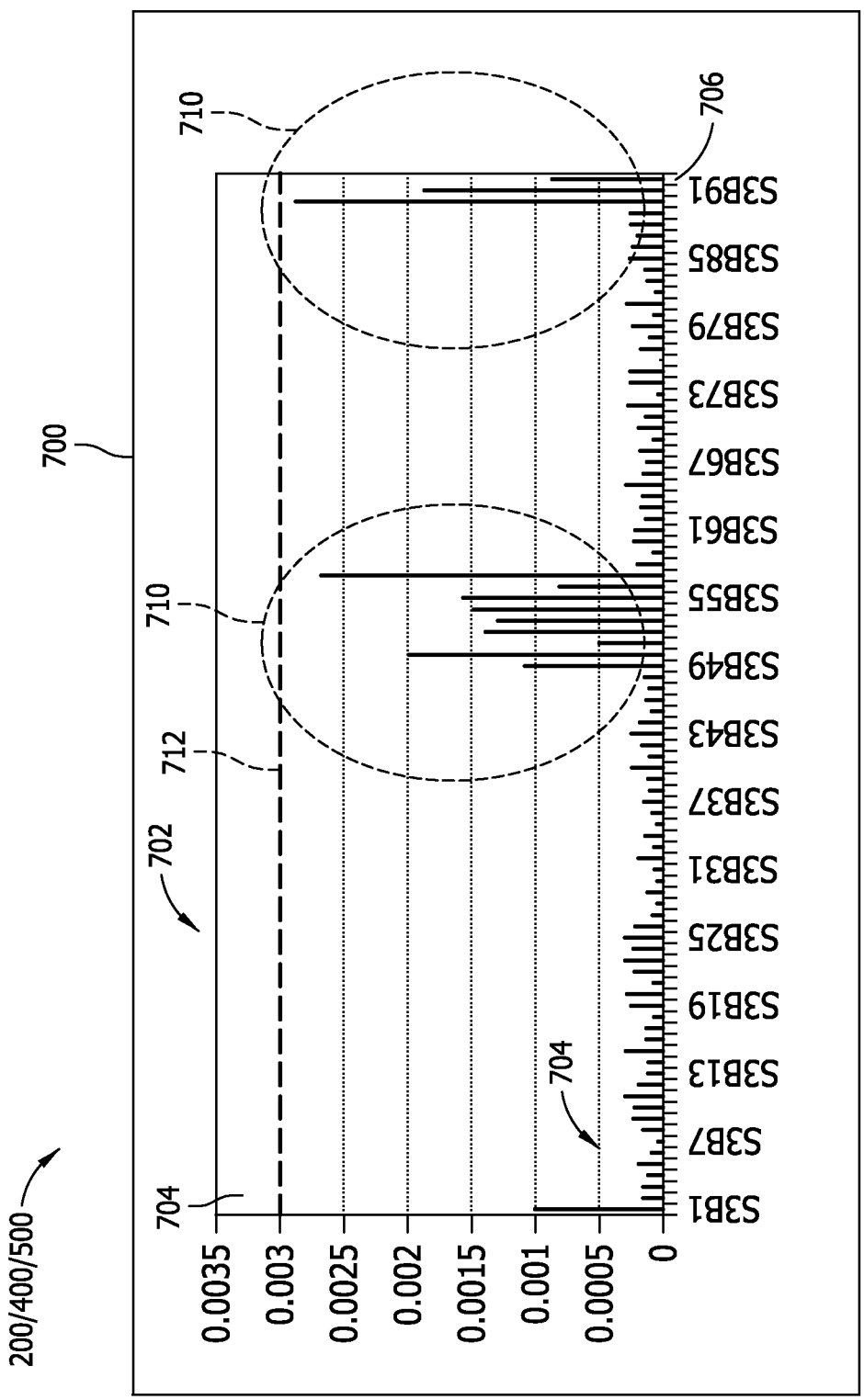
FIG. 7 is a schematic view of a monitor and an exemplary screen presentation generated by the creep life management systems shown in FIGS. 2, 4, and 5.

FIG. 7 is a schematic view of a monitor 700 and an exemplary screen presentation 702 generated by creep life management systems 200, 400, and 500, i.e., a screen view of a real-time strain profile 702. Profile 702 includes a y-axis 704 that represents strain in unitless increments of 0.0005 and an x-axis 706 that represents each of 91 buckets 124 in the third, or last stage 676 of turbine section 108 (all shown in FIG. 6). Profile 702 also includes a plurality, i.e., 91 bucket real-time strain measurements 708. Measurements 708 include two groups of elevated bucket strain measurements 710. Profile 702 further includes a strain parameter 712 having a value of 0.003. Alternatively, any incremental sizing of y-axis 704 and any value of strain parameter 712 that enable operation of systems 200, 400, and 500 as described herein are used. Also, alternatively, any number of buckets 124 in any stage of turbine section 108 and any number of blades 122 in any stage of compressor section 104 (all shown in FIG. 1) that enables operation of systems 200, 400, and 500 as described herein may be monitored.

Referring to FIGS. 6 and 7, in operation, the data collected to form a creep profile includes real-time measurements of temperature and strain on each interrogated blade 122 and bucket 124. The data are collected and stored for real-time analysis and future analysis. For example, without limitation, screen view of real-time strain profiles 702 is displayed on monitor 700 for an operator (not shown), thereby facilitating real-time monitoring of component strain.

Further, predetermined setpoints for real-time strain, for example, without limitation, a strain parameter 712 value of 0.003 may be programmed into controller 216 such that an alarm and/or warning is annunciated to alert an operator when any strain measurement 718 (shown in FIG. 7) on the monitored components approaches, attains, or exceeds such value, thereby facilitating an "early-warning" feature of creep life management systems 200, 400, and 500. For certain values of strain, e.g., without limitation, strain parameter 712, such measurements may be an input to decisioning algorithms and instructions within the programming of controller 216 (shown in FIG. 2), including, without limitation, near-term or immediate removal of engine 100 from service.

Figure 8:
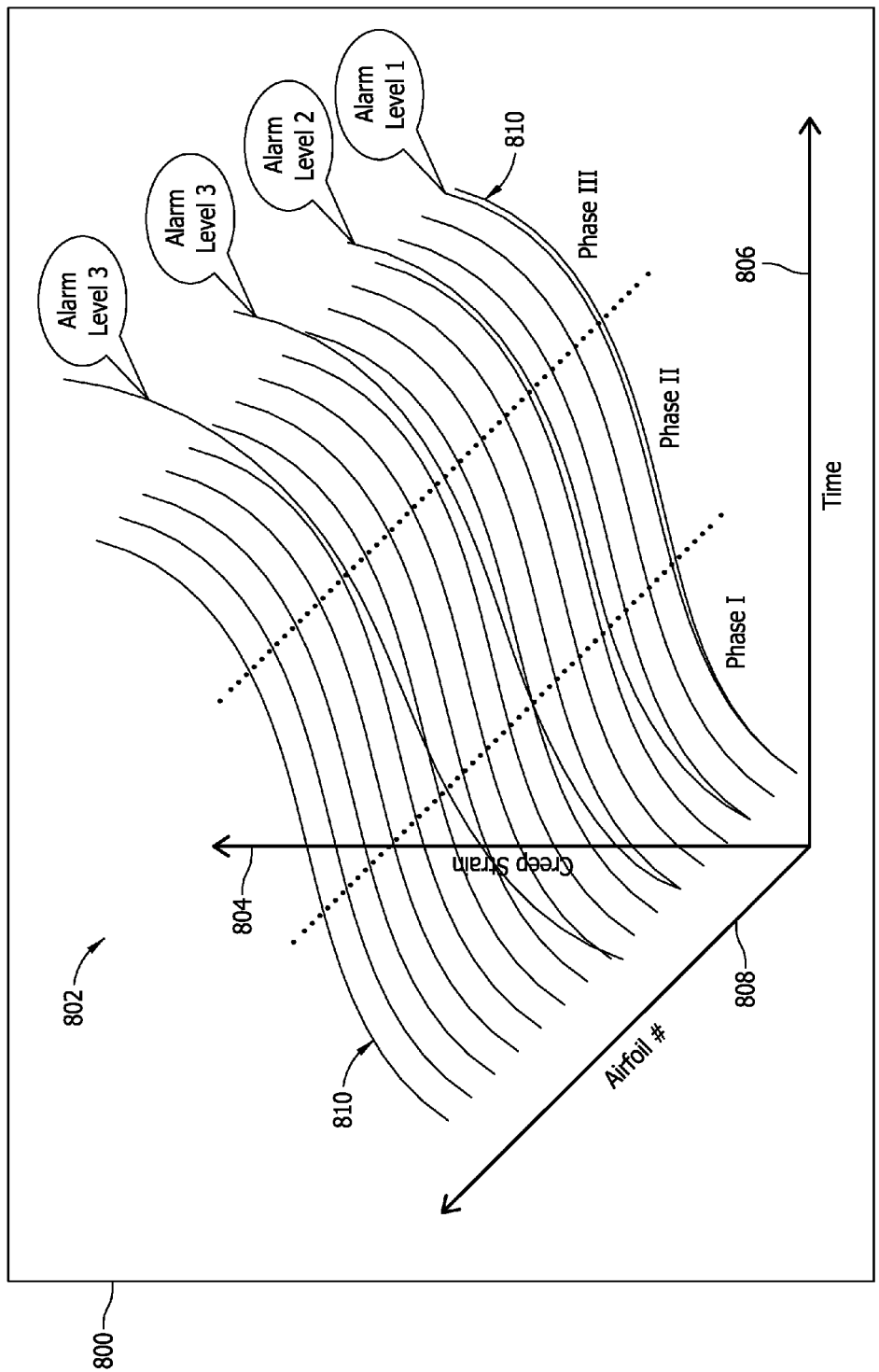
FIG. 8 is a schematic view of a monitor and another exemplary screen presentation generated by the creep life management system shown in FIGS. 2, 4, and 5.

FIG. 8 is a schematic view of a monitor 800 and another exemplary screen presentation 802 generated by creep life management systems 200, 400, and 500, i.e., a view of a real-time creep strain history profile screen 802. Profile screen 802 includes a y-axis 804 that represents typical values of creep strain. Also, profile screen 802 includes an x-axis 806 that represents time. Further, profile screen 802 includes a z-axis 808 that represents each of a plurality of blades 122 or buckets 124 (all shown in FIG. 6). Profile screen 802 also includes a plurality of individual creep strain history profiles 810 for each of the plurality of blades 122 and/or buckets 124 in gas turbine engine 100 (shown in FIG. 6). In the exemplary embodiment, a single stage of either blades 122 or buckets 124 are shown. Alternatively, any combination of individual profiles 810 for any blades 122 and any buckets 124 may be shown in profile screen 802.

Such real-time creep determinations are executed by controller 216 to generate each real-time, individual, creep strain profile 810 of the components using the known relationships between creep rate, temperature, and strain, thereby facilitating real-time monitoring of component creep rate that is integrated to determined overall component creep.

Profile screen 802 is divided into the three phases of creep history and facilitates providing an operator of gas turbine engine 100 an indication of which phase of creep is presently being exhibited by each shown blade 122 and/or bucket 124 monitored. Phase I represents the primary creep phase typically defined by an initially large creep rate that decelerates with time until it reaches a substantially minimum value. Phase II represents a secondary creep phase typically defined by a creep rate that is substantially constant at the minimum value at the end of Phase I. Phase III represents the tertiary creep phase typically defined by a creep rate that is accelerating with time. The accelerating creep rate is at least partially due to deformation of the component being monitored. Such deformation is typically an indication of impending permanent damage and component failure.

Profile screen 802 includes visual annunciation features associated with Phase III of individual creep strain history profiles 810. For example, and without limitation, a visual and/or audible Alarm Level 1 is indicative of the early stages of Phase III deformation and prompts the operator to increase the monitoring of the associated component through systems 200, 400, and 500. Also, without limitation, screen 802 includes a visual and/or audible Alarm Level 2 indicative of an accelerating rate of deformation of the monitored component and prompts the operator to make decisions with respect to increased monitoring through systems 200, 400, and 500 and possible inspection, repair, and/or replacement during the next outage. Also, Alarm Level 1 and Alarm Level 2 may prompt an operator to make operational adjustments to gas turbine engine 100 to enhance/optimize operation to facilitate extending a remaining useful life (RUL) (described further below) for each monitored and uniquely identifiable blade 122 and bucket 124.

Further, without limitation, screen 802 includes a visual and/or audible Alarm Level 3 indicative of possible near-term failure of the monitored component and prompts the operator to make decisions with respect to possible inspection, repair, and/or replacement during the next outage and near-term removal of engine 100 from service. Also, Alarm Level 3 may prompt an operator to make operational adjustments to gas turbine engine 100 to enhance/optimize operation to facilitate extending a RUL (described further below) for each monitored and uniquely identifiable blade 122 and bucket 124, at least in the short-term until engine 100 can be removed from service.

Alarm Level 3 may also be an input to decisioning algorithms and instructions within the programming of controller 216 (shown in FIG. 2), including, without limitation, near-term or immediate removal of engine 100 from service. Alternatively, screen 802 includes any number of alarm levels in any order of severity that enables operation of systems 200, 400, and 500 as described herein.

Such alarm levels, visual annunciation features, and audible annunciation features when the monitored components approach, attain, or exceed the associated parameters facilitate operation of an "early-warning" feature of creep life management systems 200, 400, and 500. For certain values of measured features, e.g., without limitation, individual creep strain history profiles 810, such measurements may be an input to decisioning algorithms and instructions within the programming of controller 216 (shown in FIG. 2), including, without limitation, near-term or immediate removal of engine 100 from service.

Figure 9:
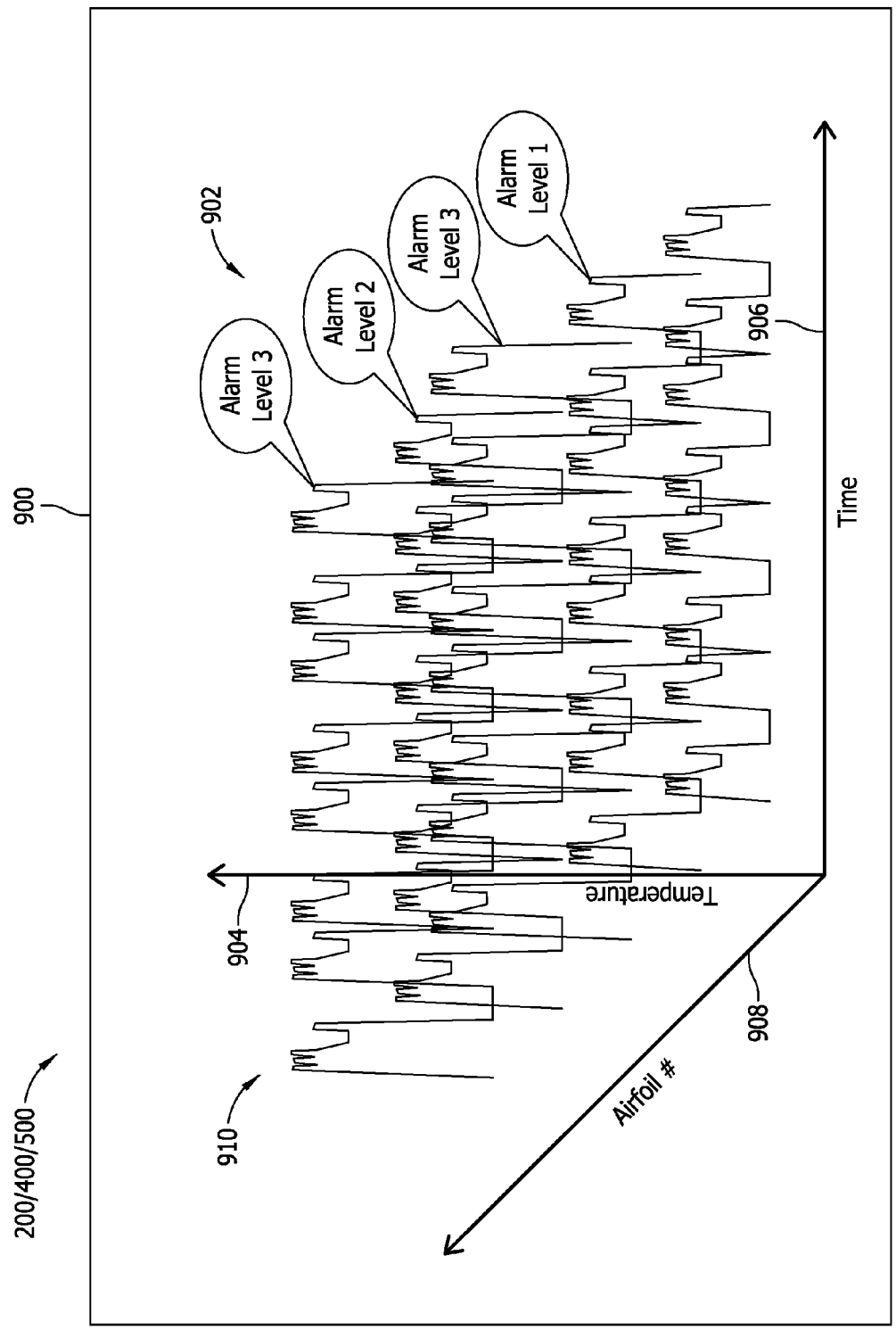
FIG. 9 is a schematic view of a monitor and yet another screen presentation generated by the creep life management system shown in FIGS. 2, 4, and 5.

FIG. 9 is a schematic view of a monitor 900 and yet another screen presentation 902 generated by creep life management systems 200, 400, and 500, i.e., a view of a real-time component temperature profile screen 902. Profile screen 902 includes a y-axis 904 that represents typical values of creep strain. Also, profile screen 902 includes an x-axis 906 that represents time. Further, profile screen 902 includes a z-axis 908 that represents each of a plurality of blades 122 or buckets 124 (all shown in FIG. 6). Profile screen 902 also includes a plurality of individual component temperature profiles 910 for each of the plurality of blades 122 and/or buckets 124 in gas turbine engine 100 (shown in FIG. 6). In the exemplary embodiment, a single stage of either blades 122 or buckets 124 are shown. Alternatively, any combination of individual profiles 910 for any blades 122 and any buckets 124 may be shown in profile screen 902.

In the exemplary embodiment, real-time component temperature profiles 910 are be displayed for each interrogated blade 122 and bucket 124. A real-time component temperature determination is executed by controller 216 to generate a real-time temperature profile of the components.

Profile screen 902 includes visual annunciation features associated with real-time component temperature profiles 910. For example, and without limitation, a visual and/or audible Alarm Level 1 is indicative of component temperatures are approaching, have attained, or have exceeded a predetermined value associated with a first predetermined setpoint for a predetermined period of time. The first predetermined temperature setpoint may be indicative of a short-term temperature excursion in engine 100 (shown in FIG. 6) and prompts the operator to increase the monitoring of the associated component through systems 200, 400, and 500. Also, without limitation, screen 902 includes a visual and/or audible Alarm Level 2 indicative of component temperatures approaching, attaining, or exceeding a predetermined value associated with a second predetermined setpoint. The second predetermined temperature setpoint may be indicative of an extended temperature excursion within engine 100 for a predetermined period of time and prompts the operator to make decisions with respect to increased monitoring through systems 200, 400, and 500 and possible inspection, repair, and/or replacement during the next outage. Also, Alarm Level 1 and Alarm Level 2 may prompt an operator to make operational adjustments to gas turbine engine 100 to enhance/optimize operation to facilitate extending a remaining useful life (RUL) (described further below) for each monitored and uniquely identifiable blade 122 and bucket 124.

Further, without limitation, screen 902 includes a visual and/or audible Alarm Level 3 indicative of component temperatures approaching, attaining, or exceeding, a predetermined value associated with a third predetermined setpoint for a predetermined period of time. The third predetermined setpoint may be indicative of possible near-term failure of the monitored component and prompts the operator to make decisions with respect to possible inspection, repair, and/or replacement during the next outage and near-term removal of engine 100 from service. Also, Alarm Level 3 may prompt an operator to make operational adjustments to gas turbine engine 100 to enhance/optimize operation to facilitate extending a RUL (described further below) for each monitored and uniquely identifiable blade 122 and bucket 124, at least in the short-term until engine 100 can be removed from service.

Alarm Level 3 may also be an input to decisioning algorithms and instructions within the programming of controller 216 (shown in FIG. 2), including, without limitation, near-term or immediate removal of engine 100 from service. Alternatively, screen 902 includes any number of alarm levels in any order of severity that enables operation of systems 200, 400, and 500 as described herein.

Such alarm levels, visual annunciation features, and audible annunciation features when the monitored components approach, attain, or exceed the associated parameters facilitate operation of an "early-warning" feature of creep life management systems 200, 400, and 500. For certain values of measured features, e.g., without limitation, real-time component temperature profiles 910, such measurements may be an input to decisioning algorithms and instructions within the programming of controller 216 (shown in FIG. 2), including, without limitation, near-term or immediate removal of engine 100 from service.

In addition to real-time creep, creep rate, temperature and strain measurements and determinations, creep life management systems 200, 400, and 500 also include history and trending features for each individual blade 122 and bucket 124 that is monitored. For example, without limitation, controller 216 is programmed to determine and display a historical temperature profile, a historical strain profile, and a historical creep profile for each individual blade 122 and bucket 124 that is monitored.

Referring to FIGS. 6, 7, 8, and 9, for example, and without limitation, strain, temperature, and creep histories for each monitored blade 122 and bucket 124 are determined from the time of installation of blades 122 and buckets 124, and/or commissioning of system 200, until the time of the latest data collection. Also, for example, and without limitation, a real-time remaining useful life (RUL) estimation for each monitored blade 122 and bucket 124 is determined from the time of installation of blades 122 and buckets 124, and/or commissioning of system 200, until the time of the latest data collection. Higher creep or temperature levels indicate that turbine engine 100 may be running hotter and might be indicative of a need to check other turbine parameters for anomalies such that early corrective actions may be taken.

Moreover, creep life management systems 200, 400, and 500 are further programmed to determine a comparison between each RUL estimation for each monitored component, wherein the comparison is at least partially representative of a prioritized order of maintenance activities for the monitored components. Also, a comparison between each RUL estimation for each monitored component and at least one predetermined RUL parameter is determined such that those components approaching an end of useful life may be "flagged" for inspection, repair, and/or replacement. Further, creep life management systems 200, 400, and 500 are further programmed to display to an operator a comparative operational history of a plurality of the monitored components, thereby facilitating identification of operating conditions that facilitate extensions of a useful life of the components.

Furthermore, in operation, the component temperature and strain data is date and time stamped such that such component data may be correlated with other operational data, including, without limitation, combustion gas temperatures. Accordingly, for those blades 122 and/or buckets 124 that have been exposed to differing operating conditions, e.g., without limitation, higher gas temperatures, as compared to similar components, components may be flagged for more frequent monitoring. Such flagged components may be selected to have a different strain warning/alarm setpoint than similar components. Also, certain components that may be more at risk than other components, e.g., without limitation, buckets 124 that do not have cooling features, may be interrogated more often. Moreover, real-time temperature and strain data for each of blades 122 and/or buckets 124 facilitates identification of those components that are "aging" more rapidly, or more slowly, than similar components in similar operating conditions with similar operating histories, and those components may be interrogated more often.

Also, for those blades 122 and/or buckets 124 that exhibit accelerated creep determinations, and/or are approaching a predetermined strain parameter, early replacement may be scheduled during planned maintenance outages. Furthermore, for those blades 122 and/or buckets 124 that have been determined to have increased frequencies of monitoring, specific inspection activities for such components may be scheduled during planned maintenance outages. Therefore, in operation, specific strain and/or creep determinations for each individual blade 122 and bucket 124 facilitates decreasing unnecessary maintenance inspections and replacements, thereby decreasing costs of operating and maintaining gas turbine engine 100.

Moreover, data collected and determined by creep life management systems 200, 400, and 500 may be used to enhance and/or calibrate physics-based models of gas turbine engine 100, including blades 122 and buckets 124. The physics-based models include details of design, construction, and operational information, such as, without limitation, component materials, component sizing and orientation, and historical gas turbine operational data. Such information and data are embodied in a finite element model (FEM) to calculate, without limitation, component stresses and temperatures, which are in turn used to estimate component RUL. With direct measurement of these values as described herein, the FEM models can be enhanced and calibrated with the collected real-time data. These enhanced and calibrated models then can be applied fleet-wide to further enhance methods of estimating RULs and enhancing the accuracy of such RUL estimates.

In contrast to known creep life management systems, the creep life management systems as described herein facilitate improving collecting and determining creep and creep-fatigue data associated with turbine engine components. Specifically, in contrast to known creep life management systems, the creep life management systems described herein include wirelessly transmitting an interrogation signal from a reader unit to a sensor apparatus having a unique identifier and wirelessly receiving measurement data for the associated component. The wireless sensor apparatus described herein are embedded and/or coupled to those components that are otherwise difficult to monitor, for example, those components rotating at high velocities and/or positioned within a harsh environment, e.g., compressor blades and turbine buckets. Therefore, real-time operational data, including temperature and strain data, may be collected in one location and stored in another location more conducive to safe, long-term storage in the reader unit, or a storage device coupled thereto. The wireless sensor apparatus described herein are passive and the energy used to power the sensor apparatus is transmitted with the interrogation signal from the reader unit, therefore no on-board power supplies are needed for the sensor apparatus. Also, each wireless sensor apparatus described herein may be individually interrogated using the unique identifier for each sensor, such unique identifier also being associated with the blade or bucket it is coupled to.

The creep life management systems as described herein facilitate determining effects of operating conditions on the service life of components over the lifetime of the components. Also, the creep life management systems as described herein facilitate better determinations of remaining service life of components, and therefore facilitate enhancing condition-based maintenance systems. Further, the creep life management systems as described may include predetermined parameters may be used to set a strain and/or temperature threshold to trigger inspection and/or replacement. Moreover, the creep life management systems as described may be used to facilitate extending inspection and replacement periodicities of those components that exhibit extended service lives. Therefore, unnecessary maintenance outages may be avoided with an easy-to-use, readily available diagnostic system, thereby facilitating a cumulative cost savings for operations and maintenance managers. Also, if patterns and/or trends of accelerated creep are determined, additional investigation may be initiated to determine the root causes. Therefore, maintenance outages may be planned to correct the root causes prior to any permanent damage, thereby further facilitating a cumulative cost savings for operations and maintenance managers.

An exemplary technical effect of the methods, systems, and apparatus described herein includes at least one of (a) wirelessly interrogating sensor apparatus coupled to components that are in harsh environments; (b) wirelessly transmitting real-time measurement data to a data repository; (c) performing real-time creep analysis of components that are in a harsh environment; (d) correlating collected measurement data to a uniquely identifiable component; (e) determining a creep profile for a component and an estimated remaining service life; (f) alerting an operator when a measured real-time strain value of a component approaches a predetermined value, attains the predetermined value, and exceeds the predetermined value; (g) directing an operator to increase monitoring of the uniquely identifiable components; (h) directing an operator to enhance/optimize operation of the turbine to facilitate extending the RUL of the uniquely identifiable components; (i) directing an operator to schedule an inspection of the uniquely identifiable components; (j) comparing each estimated remaining service life for each uniquely identifiable component to each other, thereby determining a prioritized order of maintenance activities for the uniquely identifiable components; (k) comparing each estimated remaining service life for each uniquely identifiable component to predetermined service life parameters, thereby determining a prioritized order of maintenance activities for the uniquely identifiable components; (l) generating a comparative operational history of the uniquely identifiable components, thereby facilitating identification of operating conditions that facilitate extensions of a useful life of the uniquely identifiable components; and (m) enhancing and/or calibrating physics-based models of the turbine engine and associated components using collected data to further enhance methods of estimating RULs and enhancing the accuracy of such RUL estimates.

The methods and systems described herein are not limited to the specific embodiments described herein. For example, components of each system and/or steps of each method may be used and/or practiced independently and separately from other components and/or steps described herein. In addition, each component and/or step may also be used and/or practiced with other assemblies and methods.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

While the invention has been described in terms of various specific embodiments, those skilled in the art will recognize that the invention can be practiced with modification within the spirit and scope of the claims.

What is claimed is:

1. A method of operating a turbine engine, the turbine engine including a plurality of rotatable components, at least one stationary component, and a creep life management system including a processor, an alarm component, a first portion coupled to the plurality of rotatable components, thereby defining a plurality of first portions, and a second portion coupled to the at least one stationary component, said method comprising:
   rotating the plurality of rotatable components with respect to the at least one stationary component;
   interrogating each respective first portion of the plurality of first portions by the second portion;
   transmitting from each respective first portion of the plurality of first portions a response signal in response to the interrogation by the second portion, wherein each respective response signal is representative of a measurement value of a respective rotatable component of the plurality of rotatable components;
   receiving each respective response signal at the second portion;
   determining, using the processor, a unique creep profile for each respective rotatable component of the plurality of rotatable components that is at least partially based on the respective response signal;
   determining, using the processor, a real-time remaining useful life (RUL) estimation for each respective rotatable component as a function of the response signal transmitted from each respective first portion;
   comparing, using the processor each RUL estimation for each respective rotatable component to each other to determine a prioritized order of maintenance activities for the plurality of rotatable components;
   receiving at the alarm component an alert signal transmitted by the processor, the alert signal related to at least one response signal transmitted from the plurality of sensor apparatuses; and
   performing an alert action, by the alarm component, in response to receiving the alert signal from the processor.

2. The method in accordance with claim 1, wherein determining, using the processor, a unique creep profile for each respective rotatable component comprises:
   determining the measurement value of at least one of a temperature, a strain, and a creep rate for each respective rotatable component of the plurality of rotatable components in real-time from the response signal; and
   determining a stage of creep for each respective rotatable component of the plurality of rotatable components from the measurement value.

3. The method in accordance with claim 2, wherein performing an alert action comprises alerting an operator when a real-time measurement value of at least one of the plurality of rotatable components at least one of approaches a predetermined value, attains the predetermined value, and exceeds the predetermined value.

4. The method in accordance with claim 3 further comprising facilitating operation of a condition-based maintenance system by at least one of:
   directing an operator of the turbine engine to increase monitoring of the plurality of rotatable components via the creep life management system; and
   directing an operator of the turbine engine to schedule an inspection of the plurality of rotatable components.

5. The method in accordance with claim 1, wherein determining, using the processor, a real-time remaining useful life (RUL) estimation comprises determining real-time component cumulative damage using component temperature and strain history.

6. The method in accordance with claim 5, wherein determining, using the processor, and real-time RUL estimation comprises:
   comparing each RUL estimation for each first component of the plurality of first components to at least one predetermined RUL parameter, thereby at least partially determining a prioritized order of maintenance activities for the plurality of first components; and
   displaying to an operator a comparative operational history of the plurality of rotatable components, thereby facilitating identification of operating conditions that facilitate extensions of a useful life of the plurality of first components.

7. The method in accordance with claim 1, wherein determining, using the processor, a unique creep profile comprises determining at least one of a historical temperature profile, a historical strain profile, and a historical creep profile for each respective rotatable component of the plurality of rotatable components.

8. The method in accordance with claim 1 further comprising:
   importing at least one of a historical temperature profile, a historical strain profile, a historical creep profile, and an RUL estimation for the plurality of rotatable components into at least one physics-based model of the turbine engine; and
   at least one of enhancing and calibrating the at least one physics-based model.

9. A creep life management system for a turbine engine, said system comprising:
   a plurality of sensor apparatuses, each respective sensor apparatus of said plurality of sensor apparatuses coupled to a respective rotatable component of a plurality of rotatable components of the turbine engine, wherein said each respective sensor apparatus comprises a unique identifier;

at least one reader unit coupled to a stationary component of the turbine engine, said at least one reader unit configured to transmit an interrogation request signal to said each respective sensor apparatus and receive a measurement response signal transmitted from said each respective sensor apparatus;

an alarm component, and at least one processor programmed to:
  determine a real-time creep profile for each respective rotatable component as a function of the measurement response signal transmitted from said each respective sensor apparatus;
  determine a real-time remaining useful life (RUL) estimation for each respective rotatable component as a function of the measurement response signal transmitted from said each respective sensor apparatus; and
  compare each RUL estimation for each respective rotatable component to each other to determine a prioritized order of maintenance activities for the plurality of rotatable components, wherein said alarm component is configured to:
  receive from said at least one processor an alert signal related to at least one measurement response signal transmitted from said plurality of sensor apparatuses; and
  perform an alert action in response to receiving the alert signal from the at least one processor.

10. The creep life management system in accordance with claim 9, wherein said at least one processor programmed to determine a real-time creep profile is programmed to determine at least one of a historical temperature profile, a historical strain profile, and a historical creep profile for at least one of the plurality of rotatable components.

11. The creep life management system in accordance with claim 9, wherein said alarm component configured to perform an alert action in response to receiving the alert signal from the at least one processor is configured to alert an operator when a measured real-time strain value of at least one of the plurality of rotatable components at least one of approaches a predetermined value, attains the predetermined value, and exceeds the predetermined value.

12. The creep life management system in accordance with claim 9, wherein said at least one processor is further programmed to:
  compare each RUL estimation for each rotatable component of the plurality of rotatable components to at least one predetermined RUL parameter.

13. The creep life management system in accordance with claim 9 further comprising at least one of:
  a first plurality of antennas coupled to said at least one reader unit; and
  a plurality of sensor apparatus comprising a second plurality of antennas, wherein each of said first plurality of antennas and said second plurality of antennas are positioned such that:
    a distance between each of said first plurality of antennas is at least one of:
    at least ¼ of one wavelength; and
    at least a spatial coherence distance associated with a wireless channel defined by at least one of said first plurality of antennas and at least one of said second plurality of antennas; and
    a distance between each of said second plurality of antennas is at least one of:
    at least ¼ of one wavelength; and
    at least a spatial coherence distance associated with the wireless channel defined by said at least one of said first plurality of antennas and at least one of said second plurality of antennas.

14. The creep life management system in accordance with claim 9, wherein:
  said plurality of sensor apparatuses and said at least one reader unit are coupled in wireless communication; and
  said each respective sensor apparatus comprises at least one of a strain measurement sensor and a temperature measurement sensor.

15. The creep life management system in accordance with claim 1, wherein said at least one processor is further programmed to determine a real-time component cumulative damage using component temperature and strain history.

16. A turbine engine comprising:
  a plurality of rotatable components;
  at least one stationary component; and
  a creep life management system comprising:
    a plurality of sensor apparatuses, each respective sensor apparatus of said plurality of sensor apparatuses coupled to a respective rotatable component of said plurality of rotatable components, wherein said each respective sensor apparatus comprises a unique identifier;
    at least one reader unit coupled to said at least one stationary component, said at least one reader unit configured to transmit an interrogation request signal to said each respective sensor apparatus and receive a measurement response signal transmitted from said each respective sensor apparatus;
    an alarm component; and
    at least one processor programmed to:
      determine a real-time creep profile for each respective rotatable component as a function of the measurement response signal transmitted from said each respective sensor apparatus;
      determine a real-time remaining useful life (RUL) estimation for each respective rotatable component as a function of the measurement response signal transmitted from said each respective sensor apparatus; and
      compare each RUL estimation for each respective rotatable component to each other to determine a prioritized order of maintenance activities for the plurality of rotatable components,
    wherein said alarm component is configured to:
      receive from said at least one processor an alert signal related to at least one measurement response signal transmitted from said plurality of sensor apparatuses; and
      perform an alert action in response to receiving the alert signal from the at least one processor.

17. The turbine engine in accordance with claim 16, wherein:
  said each respective sensor apparatus comprises a sensor antenna; and
  said at least one reader unit comprises a plurality of reader antennas, wherein each respective reader antenna is communicatively coupled to one or more of each said sensor antenna in one of a one-to-many relationship and a one-to-one relationship.

18. The turbine engine in accordance with claim 16, wherein:
- said each respective sensor apparatus comprises a sensor antenna; and
- said at least one reader unit comprises one reader antenna, wherein said reader antenna is communicatively coupled to each said sensor antenna in a one-to-many relationship.

19. The turbine engine in accordance with claim 16, wherein:
- said each respective sensor apparatus of said plurality of sensor apparatuses are coupled to said at least one reader unit in wireless communication; and
- said each respective sensor apparatus of said plurality of sensor apparatuses comprises at least one of a strain measurement sensor and a temperature measurement sensor.

20. The turbine engine in accordance with claim 16, wherein said plurality of sensor apparatuses and said plurality of rotatable components are positioned within at least one of a compressor section and a turbine section of said turbine engine.

* * * * *